(12) United States Patent
Irion et al.

(10) Patent No.: US 8,197,401 B2
(45) Date of Patent: Jun. 12, 2012

(54) STROBOSCOPE MODULE WITH A COUPLING

(75) Inventors: Klaus M. Irion, Emmingen-Liptingen (DE); Clemens Rebholz, Uhldingen-Muehlhofen (DE); Fritz Hensler, Neuhausen (DE); Robert Schmid, Spaichingen (DE)

(73) Assignee: Karl Storz GmbH & Co. KG (DE)

( * ) Notice: Subject to any disclaimer, the term of this patent is extended or adjusted under 35 U.S.C. 154(b) by 924 days.

(21) Appl. No.: 11/846,567

(22) Filed: Aug. 29, 2007

(65) Prior Publication Data

US 2008/0064932 A1 Mar. 13, 2008

(30) Foreign Application Priority Data

Aug. 30, 2006 (DE) .......................... 10 2006 041 950

(51) Int. Cl.
*A61B 1/06* (2006.01)
*A61B 1/00* (2006.01)
*G03B 17/00* (2006.01)
(52) U.S. Cl. ......... 600/178; 600/132; 600/180; 396/422
(58) Field of Classification Search .................. 600/154, 600/153, 112, 177, 104, 160, 182, 106, 125, 600/132, 178–180; 439/321; 411/285; 348/68, 348/75; 396/422, 424, 544
See application file for complete search history.

(56) References Cited

U.S. PATENT DOCUMENTS

| | | | | |
|---|---|---|---|---|
| 3,269,387 A | | 8/1966 | Wallace | 600/153 |
| 3,425,026 A | * | 1/1969 | Theunissen | 439/320 |
| 3,951,139 A | * | 4/1976 | Kloots | 600/249 |
| 4,842,592 A | * | 6/1989 | Caggiani et al. | 604/535 |
| 4,895,346 A | * | 1/1990 | Steigerwald | 604/247 |
| 5,101,807 A | * | 4/1992 | Kawashima | 600/112 |
| 5,147,336 A | * | 9/1992 | Wendell et al. | 604/533 |
| 5,193,135 A | * | 3/1993 | Miyagi | 385/117 |
| 5,280,975 A | * | 1/1994 | Tscheu et al. | 292/251 |
| 5,643,251 A | | 7/1997 | Hillsman et al. | |
| 7,041,054 B2 | * | 5/2006 | Klootz | 600/182 |

(Continued)

FOREIGN PATENT DOCUMENTS

DE 199 55 180 12/2000

(Continued)

OTHER PUBLICATIONS

European Search Report, Jan. 15, 2008, 6 Pages.

*Primary Examiner* — Tina My Phuong Nguyen
*Assistant Examiner* — Ryan Henderson
(74) *Attorney, Agent, or Firm* — St. Onge Steward Johnston & Reens LLC

(57) ABSTRACT

A stroboscope module has a coupling with which the stroboscope module can be connected to a light connection of an endoscope. The coupling comprises a sleeve and a base, with the base being arranged in the sleeve displacable in an axial direction between a first position and a second position. An elastically deformable cuff having an internal diameter is arranged within the sleeve, into which cuff the light connection of the endoscope can be inserted in the first position. The sleeve and the base compress the cuff in the second position such that the internal diameter of the cuff is reduced and the light connection of the endoscope is locked in the coupling. The sleeve and the base can be locked in the second position.

11 Claims, 2 Drawing Sheets

U.S. PATENT DOCUMENTS

| | | | |
|---|---|---|---|
| 2005/0240080 A1 | 10/2005 | Diekmann et al. | 600/182 |
| 2006/0020172 A1* | 1/2006 | Luerssen et al. | 600/160 |
| 2006/0074344 A1* | 4/2006 | Hibner | 600/566 |
| 2007/0092188 A1 | 4/2007 | Hoefig | 385/117 |

FOREIGN PATENT DOCUMENTS

| | | |
|---|---|---|
| DE | 10 2004 008 458 | 9/2005 |
| DE | 10 2004 052 847 | 5/2006 |
| WO | 0189598 A2 | 11/2001 |

\* cited by examiner

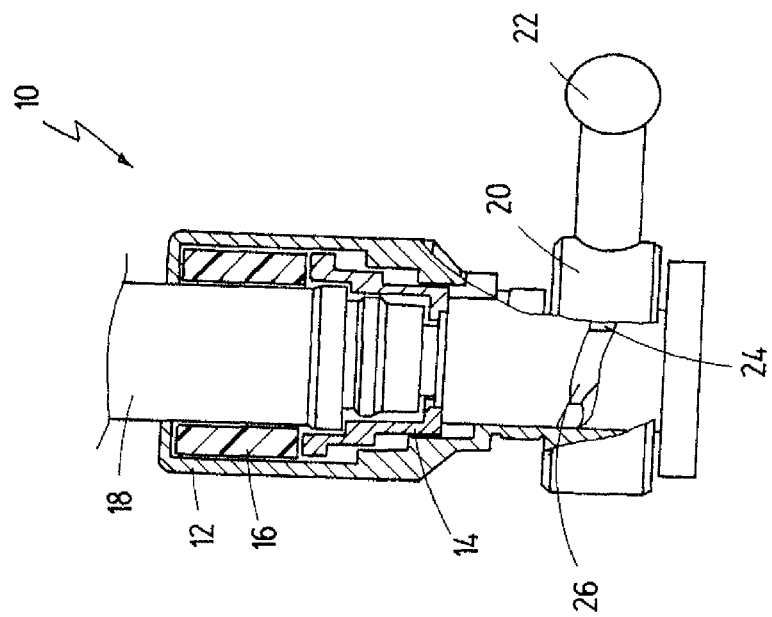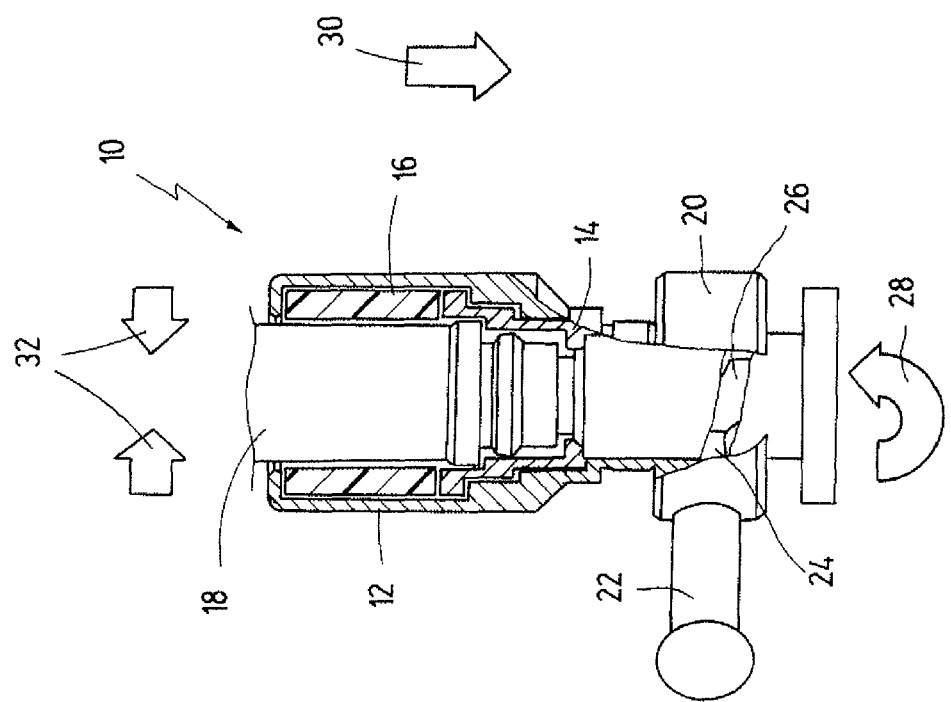

STROBOSCOPE MODULE WITH A COUPLING

BACKGROUND OF THE INVENTION

The present invention relates to a stroboscope module with a coupling with with which the stroboscope module can be connected to a light connection of an endoscope. The invention also relates to a coupling for a stroboscope module.

Stroboscopes are used in medicine, in conjunction with endoscopes, for examining the larynx. The stroboscope in this case serves to produce a stationary image of the vocal cords, which vibrate during sound production.

For examinations such as these, a stroboscope module is known, for example from DE 10 2004 052 847 A1, which combines, within one module, a stroboscopic light source, a microphone for recording sounds produced by the patient, as well as a source of electricity, a control unit for controlling the stroboscopic light source on the basis of the frequencies recorded by the microphone, and an output unit for outputting the frequencies of the sounds produced by the patient. In this document, the coupling used to connect the stroboscope module to a light connection of an endoscope is simply described as a mechanical coupling.

In the development of couplings for connecting a stroboscope module to the light connection of an endoscope, it has been found that screw connections are often disadvantageous, because even just a slight turning of the module can cause the screw connection to loosen, and the module, which is often not held by the user, to fall to the ground, resulting in damage.

Moreover, the stroboscope module should be able to be coupled to the light connection in such a way that a microphone attached to the stroboscope module can be easily oriented in the direction of the patient.

Moreover, the coupling should be configured in such a way that the stroboscope module can be coupled to the greatest possible number of different endoscopes available on the market, as far as possible independently of the design of the light connection.

Against this background, it is one object to describe a stroboscope module which comprises a coupling with which this stroboscope module can be connected easily and quickly, but at the same time reliably, to a large number of light connections of different endoscopes.

It is also an object of the invention to describe a coupling for such a stroboscope module.

SUMMARY OF THE INVENTION

The inventors have now found that the light connections of endoscopes very often have cylindrical and mostly smooth portions that can be used as an engagement point for a coupling, whereby due to this shape the engagement expediently takes place as a friction lock.

According to the invention, the object is achieved by a stroboscope module with a coupling with which the stroboscope module can be connected to a light connection of an endoscope, the coupling comprising a sleeve and a base, the base being arranged in the sleeve, the sleeve and the base being displacable relative to each other in an axial direction between a first position and a second position, an elastically deformable cuff having an internal diameter being arranged within the sleeve, into which cuff the light connection of the endoscope can be inserted in the first position, the sleeve and the base compressing the cuff in the second position such that the internal diameter of the cuff is reduced and the light connection of the endoscope is locked in the coupling, and the sleeve and the base being able to be locked in the second position.

The object is further achieved by coupling for a stroboscope module, comprising a sleeve and a base, the base being arranged in the sleeve, the base and the sleeve being displacable relative to each other in an axial direction between a first position and a second position, an elastically deformable cuff having an internal diameter being arranged within the sleeve, into which cuff a light connection of the endoscope can be inserted in the first position, the sleeve and the base compressing the cuff in the second position such that the internal diameter of the cuff is reduced and the light connection of the endoscope is locked in the coupling, and the sleeve and the base being able to be locked in the second position.

By means of such a configuration of the coupling, the light connection of an endoscope can easily be inserted into the coupling, after which the sleeve and the base are displaced relative to one another and compress the cuff. This compression of the cuff leads to a reduction in its internal diameter, as a result of which a frictional engagement is created between the cuff and the light connection, and the stroboscope module is safely secured on the light connection. Hereby, either the sleeve or the base can be connected to the stroboscope module, while the respective other component is displaceable.

This frictional engagement is maintained even when the stroboscope module is rotated, which means there is no danger of the stroboscope module falling off.

Since the stroboscope module is inserted into the cuff by a linear movement and no rotation of the stroboscope module is needed, a microphone attached to the stroboscope module can also be easily oriented with respect to the patient.

The locking in the second position can be achieved by all methods known to a man of the art. Examples of these include screw threads, bayonet-type locks, or combinations of grooves and pegs. Since the locking takes place only on the stroboscope module, and not between the endoscope and the stroboscope module, a movement of the stroboscope module no longer necessarily leads to a loosening of the connection between stroboscope module and light connection.

In a preferred embodiment of the invention, the base is connected with a force fit to the stroboscope module, and the sleeve is displaceable relative to the base.

This has the advantage, in the first instance, that this measure can be easily implemented by screwing, adhesively bonding or integrally connecting the base to the stroboscope module. Moreover, as a result of this measure, by inserting the light connection, displacing the sleeve and locking it relative to the base, the coupling can be done using one hand.

In another embodiment, the coupling comprises a coupling device with which the sleeve and the base can be moved to and fro between the first position and the second position by a rotational movement.

This has the advantage that, while at the same time holding the stroboscope module, the coupling procedure can be carried out with two fingers or, if a lever is provided on the coupling device, even with just one finger, which makes handling particularly easy.

In another embodiment of the invention, the coupling device comprises an inner thread and an outer thread, the inner thread being connected with a force fit to the sleeve and the outer thread being connected with a force fit to the base.

This embodiment, requiring simple turning-in of the threads, is simple to design and inexpensive to produce.

In an embodiment of the aforementioned measure, the inner thread and the outer thread have a pitch equal to zero in the region of the second position.

By virtue of the fact that the threads have a pitch of zero in the area of the second position, a restoring force of zero is also obtained in this area, which leads to secure locking in the second position, whereby at the same time, since there is no negative pitch to be overcome, the locking action can also be undone without having to exert any great force.

In another embodiment of the invention, the coupling device comprises a groove and a peg.

This embodiment is a structurally simple variant of the coupling device and is favourable from the point of view of production engineering.

In an embodiment of the aforementioned measure, the groove has a pitch equal to zero in the region of the second position.

This measure has the effect that the restoring force acting on the peg is equal to zero in the area of the second position, which leads to secure locking in the second position, whereby at the same time, since there is no negative pitch, the locking action can also be undone without having to exert excessive force.

In another embodiment of the invention, the cuff is made of plastic, in particular of silicone.

Plastics in general and silicone in particular are advantageous for the cuff, since they lead to a secure frictional engagement and at the same time also remain elastic over the long term.

In another embodiment of the invention, the cuff is designed as a hollow cylinder.

This has the advantage that such a cuff is easy to produce. This also results in a complete enclosure of the light connection by the cuff and, consequently, a particularly secure engagement.

In another embodiment of the invention, the coupling further comprises a light guide which, when the stroboscope module is connected to the endoscope, couples light from the stroboscope module into the light connection.

This measure considerably improves the coupling-in of light into the light connection of the endoscope.

In an embodiment of the aforementioned measure, the light guide is connected to the sleeve or to the base such that the light guide, during the movement from the first position to the second position, is displaced in the direction of the light connection.

This measure has the advantage that, when the coupling is connected to the endoscope, the light guide is brought close to the light connection, resulting in a particularly effective coupling of the light into the light connection.

It will be appreciated that the aforementioned features and those still to be mentioned below can be used not only in the respectively stated combination, but also in other combinations or on their own, without departing from the scope of the present invention.

BRIEF DESCRIPTION OF THE DRAWINGS

Exemplary embodiments of the invention are explained in more detail in the description below and are depicted in the drawings, in which:

FIG. 1 shows, partially in section, a coupling for a stroboscope module, with a light connection inserted, and in the open position, FIG. 2 shows, partially in section, the coupling for a stroboscope module from FIG. 1, with a light connection inserted, and in the closed position.

DETAILED DESCRIPTION OF PREFERRED EMBODIMENTS

Figure 3:
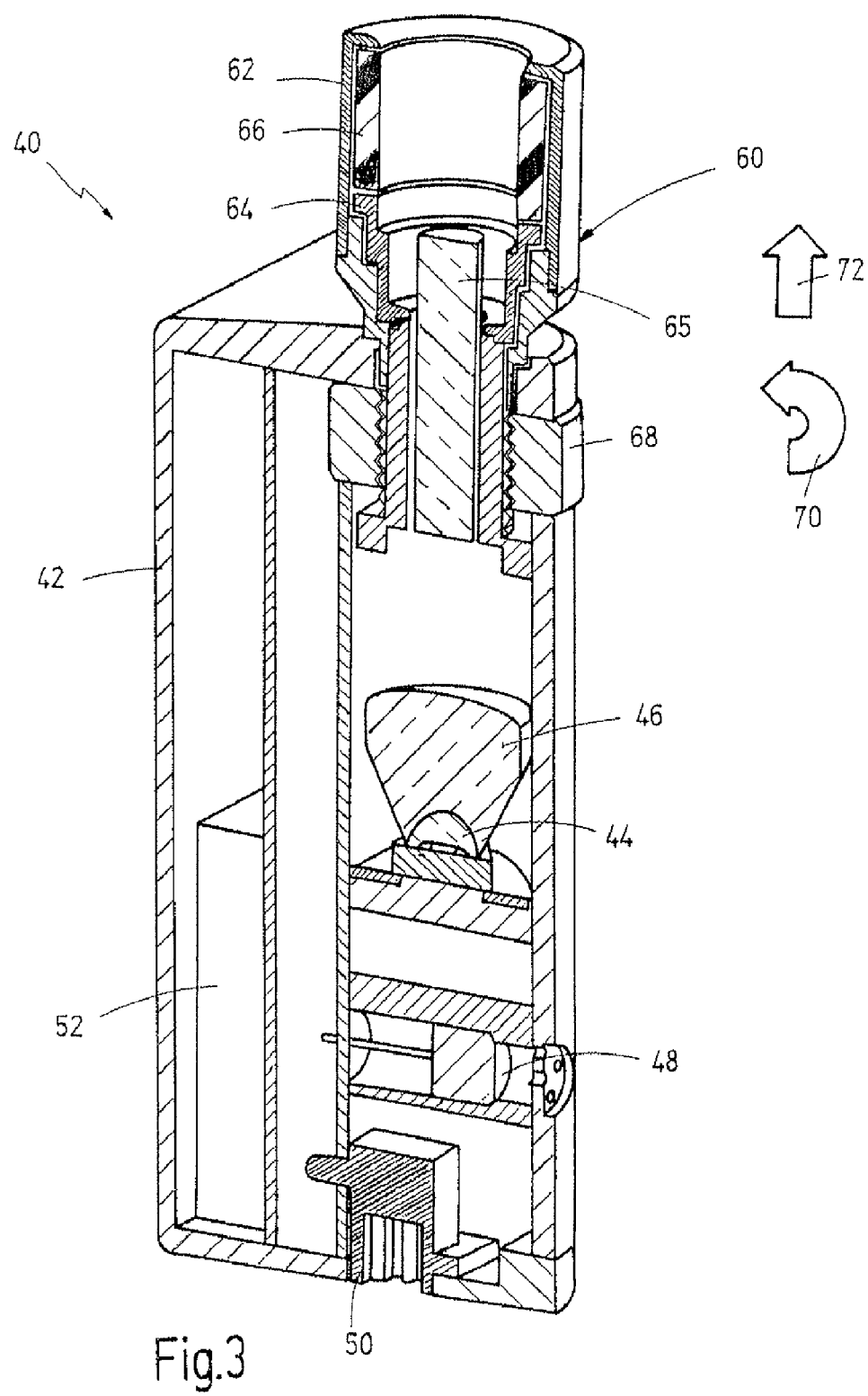
FIG. 3 shows a stroboscope module in section.

In FIG. 1, a coupling for a stroboscope module is designated in its entirety by reference number 10.

This coupling 10 comprises a sleeve 12 and a base 14, the sleeve 12 being displaceable relative to the base 14. The base 14 is in this case fixedly connected to a stroboscope module (not shown here).

A cuff 16 made of silicone rubber and in the form of a hollow cylinder is arranged between the sleeve 12 and the base 14. The cuff 16 is enclosed along its outer circumferential surface by the sleeve 12, whereby, at its upper end, the sleeve 12 partially encloses the upper end face of the cuff 16.

A light connection 18 of an endoscope (not shown here) is inserted into the interior of the cuff 16 and thus also into the sleeve 12.

The coupling 10 also comprises a nut 20, which is mounted such that it can be rotated about the base 14 by means of a handle 22 and which is connected to the sleeve 12 with a force fit, but is able to be rotated relative to it.

The nut 20 further comprises a peg 24, which engages in a helical groove 26 in the base 14. These form a coupling device with which the linear movement of the sleeve 12 relative to the base 14 can be brought about by a rotational movement.

To secure the stroboscope module to the light connection 18 of an endoscope, the light connection 18 is inserted into the cuff 16. Thereafter, the nut 20 is turned in the direction of the arrow 28 by means of the handle 22, with the peg 24 following the helical groove 26. The rotational movement of the nut 20 is in this way converted into a linear movement in the direction of the arrow 30. In this way, the sleeve 12 and the base 14 are transferred from the first position to the second position.

By virtue of the force-fit connection between the nut 20 and the sleeve 12, the sleeve 12 is moved downwards in the direction of the arrow 30. Since the sleeve 12 partially encloses the upper end face of the cuff 16, the cuff 16 is pressed by the sleeve 12 onto the base 14 and deforms. In doing so, the cuff 16 expands in the direction of the two arrows 32 in the direction of its interior, as a result of which the internal diameter of the cuff 16 is reduced and frictional engagement between the cuff 16 and the light connection 18 is obtained.

Since the sleeve 12 encloses the outer circumferential surface of the cuff 16, an outward expansion of the cuff 16 is effectively avoided. In the state after these movements, shown in FIG. 2, the frictional engagement between the cuff 16 and the light connection 18 ensures that the coupling 10 is connected to the light connection 18 in the longitudinal direction and also secure against rotation. In this way, a stroboscope module can be correctly oriented and safely connected to a light connection 18 of an endoscope.

In FIG. 3, a stroboscope module is designated in its entirety by reference number 40.

The stroboscope module 40 comprises a housing 42, in which an LED 44 is arranged with a focussing lens 46 in front of it. These form the stroboscopic light source.

The housing 42 also accommodates a microphone 48, which is used to record a sound made by a patient. This microphone 48 is connected to the external environment via holes formed in the housing 42.

At the bottom of the stroboscope module 40 there is a connector 50, which can be used either for charging a lithium ion accumulator 52 or for supplying the stroboscope module 40 directly with electricity.

During operation, the microphone 48 picks up a sound produced by a patient and forwards this sound to a control unit (not shown here) which, depending on the frequency of this sound, triggers the LED 44, which optionally emits continuous light or pulsed light, whereby the frequency of the pulsed light is dependent on the frequency of the sound produced by the patient. The control unit (not shown here) can also display the frequency of the emitted sound on a display element (also not shown here).

At the upper portion of the housing 40, a coupling 60 is arranged above the LED 44.

This coupling 60 comprises a sleeve 62 and a base 64, with the interior of the base 64 containing a light guide in the form of a quartz rod 65, which serves to focus the light emitted from the LED 44 and the focussing lens 46 into a light guide of an endoscope. Between the sleeve 62 and the base 64 there is once again arranged a cuff 66 in the form of a hollow cylinder made from an elastic plastic.

The coupling 60 also comprises a nut 68, which is connected via an inner thread to an outer thread of the base 64.

If the nut 68 is now turned in the direction of the arrow 70, the inner thread of the nut 68 engages in the outer thread of the base 64 and displaces it upwards in the direction of the arrow 72. In this way, the cuff 66 is pressed against the sleeve 62 (which encloses the cuff at the upper end thereof) and is deformed. On completion of this rotational movement, both the inner thread of the nut 68 and also the outer thread of the base 64 have a pitch equal to zero, as a result of which the base 64 is locked in this position. When a light connection of an endoscope is inserted into the coupling 60, the deformation of the cuff 66 leads to a frictional engagement between the light connection and the cuff 66, as a result of which the stroboscope module 40 is securely connected to the light connection and, therefore, to the endoscope.

Since the quartz rod 65 is connected to the base 64, it too is displaced upwards in the direction of the arrow 72, that is to say in the direction of the light connection (not shown here). In the state of connection to the endoscope, the quartz rod is arranged such that it comes to lie at a distance of 0.7 mm in front of an endpiece of the light connection, thereby ensuring a particularly effective coupling of light from the stroboscope module into the light connection.

What is claimed is:

1. A stroboscope module with
    a coupling with which said stroboscope module can be connected to a light connection of an endoscope, said coupling comprising a sleeve and a base,
    said base being arranged in said sleeve,
    said sleeve and said base being displaceable relative to each other in an axial direction between a first position and a second position,
    an elastically deformable cuff having an internal diameter being arranged within said sleeve, into which cuff said light connection of said endoscope can be inserted in said first position,
    said sleeve and said base compressing said cuff in said second position such that said internal diameter of said cuff is reduced and said light connection of said endoscope is locked in said coupling, and
    said sleeve and said base being able to be locked in said second position, a light guide which, when said stroboscope module is connected to said endoscope, couples light from said stroboscope module into said light connection,
    said light guide being connected to said sleeve or to said base such that said light guide, during a movement from said first position to said second position, is displaced in the direction of said light connection.

2. The stroboscope module of claim 1, wherein said base is connected with a force fit to said stroboscope module, and said sleeve is displaceable relative to said base.

3. The stroboscope module of claim 1, wherein said coupling comprises a coupling device with which said sleeve and said base can be moved to and fro between said first position and said second position by a rotational movement.

4. The stroboscope module of claim 3, wherein said coupling device comprises an inner thread and an outer thread, said inner thread being connected with a force fit to said sleeve and said outer thread being connected with a force fit to said base.

5. The stroboscope module of claim 4, wherein said inner thread and said outer thread have a pitch equal to zero in a region of said second position.

6. The stroboscope module of claim 3, wherein said coupling device comprises a groove and a peg.

7. The stroboscope module of claim 6, wherein said groove has a pitch equal to zero in a region of said second position.

8. The stroboscope module of claim 1, wherein said cuff is made of plastic.

9. The stroboscope module of claim 8, wherein said cuff is made of silicone.

10. The stroboscope module of claim 1, wherein said cuff is designed as a hollow cylinder.

11. A coupling for a stroboscope module, comprising a sleeve and a base,
    said base being arranged in said sleeve, said base and said sleeve being displaceable relative to each other in an axial direction between a first position and a second position,
    an elastically deformable cuff having an internal diameter being arranged within said sleeve, into which cuff a light connection of said endoscope can be inserted in said first position,
    said sleeve and said base compressing said cuff in said second position such that said internal diameter of said cuff is reduced and said light connection of said endoscope is locked in said coupling, and
    said sleeve and said base being able to be locked in said second position,
    a light guide which, when said coupling is connected to an endoscope, couples light from said coupling into a light connection,
    said light guide being connected to said sleeve or to said base such that said light guide, during a movement from said first position to said second position, is displaced in the direction of said light connection.

* * * * *